(12) United States Patent
Steindler et al.

(10) Patent No.: US 6,638,763 B1
(45) Date of Patent: Oct. 28, 2003

(54) ISOLATED MAMMALIAN NEURAL STEM CELLS, METHODS OF MAKING SUCH CELLS

(75) Inventors: Dennis A. Steindler, Memphis, TN (US); Eric D. Laywell, Memphis, TN (US); Valery G. Kukekou, Memphis, TN (US); L. Brannon Thomas, Johnson City, TN (US)

(73) Assignee: University of Tennessee Research Foundation

( * ) Notice: Subject to any disclaimer, the term of this patent is extended or adjusted under 35 U.S.C. 154(b) by 0 days.

(21) Appl. No.: 09/402,227

(22) PCT Filed: Jan. 7, 1998

(86) PCT No.: PCT/US98/00366

§ 371 (c)(1), (2), (4) Date: Oct. 1, 1999

(87) PCT Pub. No.: WO98/30678

PCT Pub. Date: Jul. 16, 1998

Related U.S. Application Data

(60) Provisional application No. 60/034,910, filed on Jan. 7, 1997.

(51) Int. Cl.$^7$ ................................................. C12N 5/08
(52) U.S. Cl. ....................... 435/368; 435/377; 435/384; 435/325
(58) Field of Search ................................ 435/325, 377, 435/378, 379, 383, 384, 395, 402, 368

(56) References Cited

U.S. PATENT DOCUMENTS

| | | | | |
|---|---|---|---|---|
| 5,411,883 A | * | 5/1995 | Boss et al. .................. 435/240 |
| 5,753,506 A | * | 5/1998 | Jobe ............................ 435/377 |
| 5,851,832 A | * | 12/1998 | Weiss et al. ................. 435/368 |
| 5,891,636 A | | 4/1999 | Van Gelder et al. ............ 435/6 |

FOREIGN PATENT DOCUMENTS

| | | |
|---|---|---|
| WO | WO98/30678 | 1/1997 |

OTHER PUBLICATIONS

Blass–Kampmann et al., J. Neuroscience Research, 37:359–373, 1994.*
Scheffler et al., TINS, 22:348–357, 1999.*
Svendsen et al., TINS, 22:357–364, 1999.*
Sanberg et al., Nucleic Acids Symposium Series, No. 38, pp. 139–142, 1998.*
Alvarez–Buylla, A. and Lois C., Neuronal stem cells in the brain of adult vertebrates,: Stem Cells, 13:263–272, 1995.
Anderson and Waxman, Ann. N.Y. Acad. Sci., 457:213–233, 1985.
Brustel, Maskos and McKay, "Host–guided migration allows targeted introduction of meurons into the embryonic brain," Neuron, 15:1275–1285, Dec., 1995.

Cattaneo and McKay, "Proliferation and differentiation of neuronal stem cells regulated by nerve growth factor," Nature, 347:762, Oct. 25, 1990.
Chiasson, Tropepe, Morshead, and van der Kooy, J. Neurosci., 19:4462–4471, Jun. 1, 1999.
Doetsch, Caille, Lim, Garcia–Verdugo, and Alvarez–Buylla, "Subventricular zone astrocytes are neural stem cells in the adult mammalian brain," Cell, 97:703–716, Jun. 11, 1999.
Fillmore, Gates, Thomas, Schweitzer and Steindler, "A novel method to culture the subependymal zone of the adult rodent reveals immature neurons that prefer an environment rich in extracellular matrix molecules," Neurosci Abs., 21:1528, 1995.
Friedrich and Soriano, "Promotor traps in embryonic stem cells: A genetic screen to identify and mutate developmental genes in mice," Genes Dev., 5:1513–1523, 1991.
Gage, Fred H., Ray, Jasodhara and Fisher, Lisa J., Isolation, Characterization And Use Of Stem Cells From The CNS,: Ann. Rev. Neurosci., 18:159–192, 1995.
Gates, Laywell, Fillmore and Steindler, "Astrocytes and extracellular matrix in adult mice following intracerebral ganglionic eminence," Neuroscience, 74:579–597, 1996.
Gates et al., "Cell and molecular analysis of the developing and adult mouse subventricular zone of the cerebral hemispheres," J. Comp. Neurol., 361:249–266, 1995.
Gritti et al., "Multipotential stem cells from the adult mouse brain proliferate and self–renew in response to basic fibroblast growth factor," J. Neurosci., 16:1091–1100, Feb. 1, 1996.
Herrington, "Effect of disulfide–bond reducing agents on the specific binding of growth hormone to microsomal membrane preparations from rabbit liver," Biochem. Pharmacol., 35(8):1359–1364, 1986.
Jankovski et al., J. Comp. Neurol., 371:376, 1996.
Johansson, Momma, Clarke, Risling, Lendahl, and Frisén, "Identification of a neural stem cell in the adult mammalian central nervous system," Cell 96:25–34, Jan. 8, 1999.
Kirschenbaum and Goldman, "Brain–derived neurotrophic factor promotes the survival of neurons arising from the adult rat forebrain subependymal zone," Proc. Nat'l. Acad. Sci., USA, 92:210–214, Jan. 1995.
Kirschenbaum et al., "In vitro neuronal production and differentialtion by precursor cells derived from the adult human forebrain," Cerebral Cortex, 6:576–589, Nov./Dec. 1994.

Primary Examiner—Lorraine Spector
Assistant Examiner—Robert C. Hayes
(74) Attorney, Agent, or Firm—Akerman Senterfitt; Stanley A. Kim

(57) ABSTRACT

Using a novel culture approach, previously unknown populations of neural progenitor cells have been found within an adult mammalian brain. By limiting cell-cell contact, dissociated adult brain yields at least two types of cell aggregates. These aggregates or clones of stem/precursor cells can be generated from adult brain tissue with significantly long postmortem intervals. Both neurons and glia arise from stem/precursor cells of these cultures, and the cells can survive transplantation to the adult mammalian brain.

1 Claim, 7 Drawing Sheets

OTHER PUBLICATIONS

Figure 1:
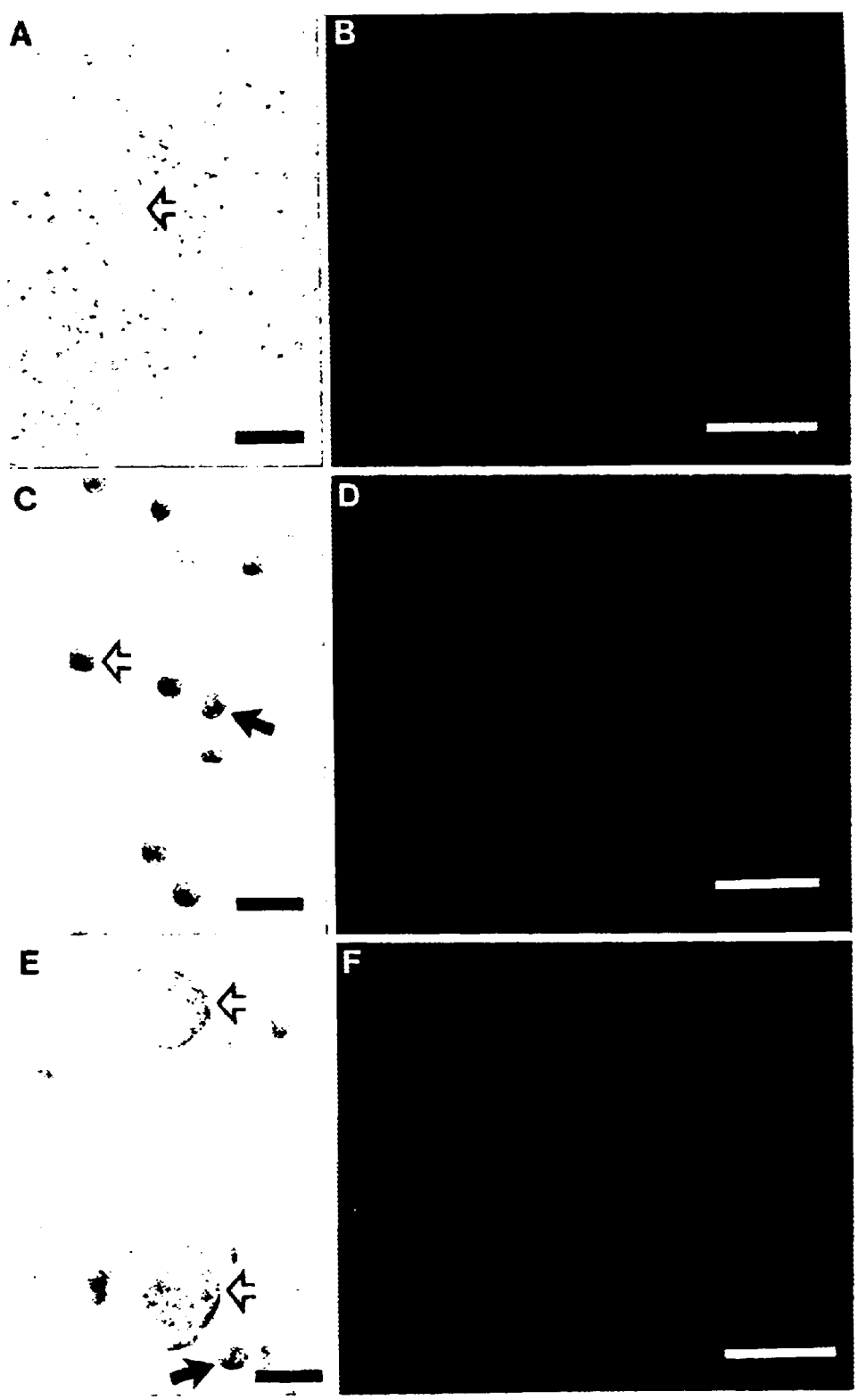

Klein, Beck and Miller, "Tenascin Is A Cytoadhesive Extracellular Matrix Component Of The Human Hematopoitic Microenvironment," *J. Cell Biol.*, 123:1027–1035, Nov. 1993.

Kukekov VG, Laywell ED, Thomas LB, and Steindler DA, "A Nestin–Negative Precursor Cell From The Adult Mouse Brain Gives Rise To Neurons And Glia," *Glia*, 21(4):399–407, Dec. 1997.

Larochelle et al., "Identification of primitive human hematopoietic cells capable of repopulating NOS/SCID mouse bone marrow:Implications for gene therapy," *Nature Med.*, 2:1329–1337, Dec. 1996.

Laywell et al., *Neurosci Abs.*, 232:297, 1997.

Levison and Goldman, "Both oligodendrocytes and astrocytes develop from progenitors in the subventricular zone of postnatal rat forebrain," *Neuron*, 10:302–212, 1993.

Luskin, "Restricted proliferation and migration of postnatally generated neurons derived from the forebrain subventricular zone," *Neuron*, 11:173–189, Jul. 1993.

Menezes and Luskin, "Expression of neuron–specific tubulin defines a novel population in the proliferative layers of the developing telencephalon," *J. Neurosci.*14:5399–5416, Sep. 1994.

Molowny, Nacher, and Lopez–Garcia, *Neuroscience*, 68(3):823–836, 1995.

Morshead et al., "Neural stem cells in the adult mammalian forebrain: A relatively quiescent subpopulation of subependymal cells," *Neuron*, 13:1071–1082, Nov. 1994.

Potten and Loeffler, "Stem cells: Attributes, cycles, spirals, pitfalls, and uncertainties. Lessons for and from the crypt," *Development*, 110:1001–1020, 1990.

Reynolds and Weiss, "Clonal and population analyses demonstrate that an EGF–responsive mammalian embryonic CNS percursor is a stem cell, "*Dev. Biol.*, 175:1–13, 1996.

Reynolds and Weiss, "Generation of neurons and astrocytes from isolated cells of the adult mammalian central nervous system," *Science*, 255:1707–1710, Mar. 27, 1992.

Reynolds, Tetzlaff and Weiss, "A multipotent EGF–responsive atriatal embryonic progenitor cell produces neurons and astrocytes," *J. Neurosci.*, 12:4565–4574, Nov. 1992.

Richards, Kilpatrick and Bartlett, "De novo generation of neuronal cells from the adult mouse brain," *Proc. Nat'l, Acad. Sci. USA*, 89:8591–8595, Sep. 1992.

Steindler, Dennis A.; Kadrie, Tareck; Fillmore, Helen and Thomas, L. Brannon; "The Subependymal Zone: 'Brain Marrow'," *Prog. Brain Res.*, 108:349–363, 1996.

Thomas, Gates and Steindler, "Young neurons from the adult mouse subependymal zone migrate and proliferate along an astrocyte, extracellular matrix–rich pathway," *Glia*:17:1–14, 1996.

Vescovi, Reynolds, Fraser and Weiss, "bFGF regulates the proliferative fate of unipotent (neuronal) and bipotent (neuronal/astroglial) EGF–generated CNS progenitor cells," *Neuron*, 11:951–966, 1993.

Weiss, Dunne, Hewson, Wohl, Wheatly, Peterson, and Reynolds, "Multipotent CNS stem cells are present in the adult mammalian spinal cord and ventricular neuroaxis," *J. Neurosci.*, 16:7599–7609, Dec. 1, 1996(a).

Weiss, Reynolds, Vescovi, Morshead, Craig and van der Kooy, "Is there a neural stem cell in the mammalian forebrain?" *Trends Neurosci.*, 19(9):387–393, 1996(b).

Yoder and Williams, "Matrix molecule interactions with hematopoietic stem cells," *Exp. Hematol.*, 23:961–967, 1995.

Zerlin, Levison and Goldman, Early patterns of migration, morphogenesis, and intermediate filament expression of subventricular zone cells in th epostnatal rat forebrain. *J. Neurosci.*, 15:7238, Nov. 1995.

* cited by examiner

ISOLATED MAMMALIAN NEURAL STEM CELLS, METHODS OF MAKING SUCH CELLS

This application is the National Stage of International Application No. PCT/US98/00366 filed Jan. 7, 1998, which claims priority of, and incorporates by reference in its entirety, U.S Provisional Application Ser. No. 60/034,910 filed Jan. 7, 1997.

This research has been partially funded by a United States federal grant from the National Institutes of Health, Grant Number: NIH/NINDS 1R01NS29225. The United States Government may, therefore, have certain rights to this invention.

1. FIELD OF THE INVENTION

This invention relates generally to novel mammalian brain cell types and methods of culturing such cells. The methods of the instant invention, which utilize suspension cultures and factors that limit cell contacts, result in an amplification of the production of neural stem and progenitor cells, and clones of such cells, from the adult mammalian brain, including the human brain and from tissue with significant (e.g. 1 day) postmortem intervals. Propagation of neural stem and progenitor cells is relevant to the large-scale production of glial and neuronal cells, and clones of such cells, as well as self-repair of the brain in neurological disease.

2. DESCRIPTION OF THE RELATED ART

Prior to the present invention, cells from numerous tissues have been described that have attributes of stem or germ cells (i.e., spermatozoon or an ovum), and that are extremely well-suited for rapid self-renewal. Brain-derived stem cells have only recently been a major focus of attention, using a variety of lineage tracing and culture methodologies. See for example, Gage et al., Ann. Rev. Neurosci., 18:159–192 (1995); Svendsen et al., Trends Neurosci., 18:465–467 (1995); Alvarez-Buylla et al., Stem Cells, 13:263–272 (1995); Weiss et al., Trends Neurosci., 19:387–393 (1996); Steindler et al., Prog. Brain Res., 108:349–363 (1996); and Brustle et al., Neuron, 15:1275–1285 (1995).

Previous studies showed the presence of a dense extracellular matrix ("ECM") on and around subependymal zone ("SEZ") cells of the adult rodent (see, Gates et al., J. Comp. Neurol., 361:249–266 (1995); and Thomas et al., Glia, 17:1–14 (1996)). ECM molecules may facilitate cell movement and aspects of differentiation during development, and they are also implicated in a number of neuropathological conditions. Glycoproteins such as tenascin-C (TN) and proteoglycans such as the chondroitin sulfate-containing proteoglycans (CSPG) are expressed in high levels in the young brain, where they seem to have a role in forming glycoconjugate-rich boundaries around different functional groups of neurons, such as the somatosensory whisker barrel fields and striosomes in the striatum. They are then down-regulated in later stages of development (e.g. postnatal days 14–21) and normal adulthood, but their expression is enhanced in neuropathologic conditions, such as traumatic brain injury, where they are an important component of glial scar formation. In the astroglial/mesonchymal scar, they may create a barrier that inhibits the growth of neurites into the scar, although it has been proposed that some ECM molecules may actually encourage neuritic growth under some circumstances. It has also been suggested that ECM molecules regulate cell proliferation, differentiation, migration, and survival through cell-cell and cell-ECM interactions. Stem cells have been described in embryonic and postnatal mouse brain and in proliferative "neurospheres" that can be harvested and cultured from different brain areas, including the developing subventricular zone. See, for example, Cattaneo et al., Nature 347:762 (1990); Richards et al., Proc. Nat'l Acad. Sci. (USA), 89:8591–8595 (1992); Reynolds et al., Science, 255:1707–1710 (1992); Reynolds et al., J. Neurosci. 12:4565–4574 (1992); Reynolds et al., Dev. Biol., 175:1–13 (1996); Vescovi et al., Neuron, 11:951–966 (1993); Kirschenbaum et al., Cerebral Cortex, 6:576–589 (1994); Kirschenbaum et al., Proc Nat'l Acad. Sci. (USA), 92:210–214 (1995) Fillmore et al., Neurosci Abs., 21:1528 (1996); and Gritti et al., J. Neurosci., 16:1091–1100 (1996). Evidence from immunolabeling and cell birthday analyses has pointed to the existence of such cells in the adult SEZ. See, for example, Luskin et al., Neuron, 11:173–189 (1993); Menezes et al., J. Neurosci. 14:5399–5416 (1994); Levison et al., Neuron. 10:201–212 (1993); Gates et al., J. Comp. Neurol., 361:249–266 (1995), Zerlin et al., J. Neurosci. 15:7238 (1995); Thomas et al., Glia, 17:1–14 (1996); and Jankovski et al., J. Comp. Neurol., 371:376 (1996). The combination of stem/precursor cells, and a dense ECM in the peri-ventricular SEZ throughout the neuraxis has prompted the inventors of the instant invention to refer to this area as being the neuropoietic "Brain Marrow" (Steindler et al, Pros. Brain Res. 108: 349, (1996)) since it contains elements in common with hematopoietic bone marrow.

In addition, it has recently been described that small numbers of neurons were found to arise from precursor cells of adult human temporal lobe (Kirschenbaum et al., Cerebral Cortex, 6:576–589 (1994), Laywell et al., Neurosci. Abs. 23:297 (1997)). The production of proliferating progenitor cells from the adult rodent brain and spinal cord has also been recently described (see, Gritti et al., J. Neurosci., 16:1091–1100 (1996); and Weiss et al., J. Neurosci., 16,7599–7609 (1996)). This is surprising in that with few exceptions, neuronogenesis has traditionally been thought to end shortly after birth in the mammalian central nervous system (CNS) (see, Gage et al., Ann. Rev. Neurosci. 18:159–192 (1995)). The possibility that multipotential stem cells persist in the adult brain has implications for neuroregeneration and CNS transplantation. Accordingly, there is a need in the art for such technology. This need is met by the present invention.

The present invention discloses an advancement in the biological arts in which previously unknown brain stem cells are cultured and isolated. The brain stem cells are characterized in that the daughter cells of the brain stem cells differentiate into neurons and glia and, therefore, are useful in neuroregeneration cell biology, and CNS drug-effects and drug-discovery studies. The novel method of isolating such cells comprises culturing dissociated adult mammalian brain in conditions that affect cell-substrate and cell-cell contacts. The cultured aggregates survive transplantation to the adult mammalian brain. Following transplantation, the daughter cells of the transplanted stem cells differentiate into other cell types, including but not limited to glia, neurons, astrocytes, and oligodendrocytes, thus allowing for replacement of cells damaged by injury or disease.

Studies of the ECM molecules in the adult brain revealed the existence of an ECM-rich pathway within which neuronal progenitor cells proliferate and migrate. These ECM molecules play a significant role in these events. According to the invention, the in vitro manipulation of these and related molecules affects cellular adhesity to other cells or substrates, and affects the growth of neural stem and progenitor cells, as described below.

To discourage cell-cell interactions that induce cellular differentiation, and thus contribute to an increased cellular proliferation of stem/progenitor cells, dissociated cells from the adult brain were cultured in factors that interfere with protein-protein interactions, or in gelatinous organic substances that also discourage cell contacts and allow the isolation of clonally-related colonies (spheres) of cells. There is a great expansion of the numbers of adult brain stem and progenitor cells due to these conditions, with potentially up to millions of neuronal and glial progenitors from small numbers of founder cells in less than three months. When aggregates of progenitor cells are plated on particular extracellular matrix molecule substrates in the presence of different growth factors, hormones, steroids, and other factors (see, Examples 3, and 10), they differentiate into neurons and glial cells. Such cells are suitable for studies of drug-discovery and testing using clones of glial and neuronal cells as well as for cell replacement therapies in a variety of brain structures (e.g. in the brain or spinal cord for regeneration or space-occupation, as in spinal cord syrinx injuries, or stroke cavities, arteriovenous malformations, epileptic foci, or peripheral nerve neuromas).

Stem cells appear to make up 0.001–0.01% of an entire population of cells in renewing or potentially renewing tissues such as bone and "brain marrow" (see, Thomas et al., *Glia,* 17:1–14 (1996)). Hence, any method that assures a large scale production of differentiated cells from a small number of the most primitive stem/precursor cells is extremely useful for self-repair (autologous cell replacement) therapies following traumatic or degenerative disease. The invention harvests brain cells from a variety of sources including, but not limited to, rodent brain specimens, human brain biopsy, and post-mortem mammalian brain tissue. The invention method includes isolation and amplification of neural cells as a therapeutic self-repair approach for neurological disease, particularly human disease. To accomplish the isolation and amplification, the present invention uses a novel tissue culture approach to maximize the isolation of stem cells, and to assure a maximal number of transplantable cells from a very small number of stem cells, thus assuring the least risk for complications from a targeted and small biopsy site. At the same time, the culture method offers the possibility for large scale cell production from a very limited number of extracted stem cells. Furthermore, since a more primitive type of stem/precursor cell, than any seen prior to now, has been isolated and expanded using the invention technology, this cell type is more amenable to central nervous system (CNS) transplantation and integration, as well as gene transduction approaches. For example, using various vectors, the isolated cells of this invention can be transduced with genes coding for desired functions. For example, vectors containing genes coding for adhesion molecules can be transduced into these cells to increase cellular adhesivity. This would be useful, for example, to produce glia with increased adhesivity for cavity-filling approaches. Alternatively, the isolated cells of the present invention can be transduced with genes coding for growth factors and directing neuronal phenotype, including neurotransmitter associated genes to produce neurons capable of increased neurotransmitter production. In addition, because the cells of the present invention are pluripotent, they are extremely well suited for cell-grafting approaches.

It is to be understood that both the foregoing general description and the following detailed description are exemplary and explanatory and are intended to provide further explanation of the invention as claimed. Other objects, advantages and novel features will be readily apparent to those skilled in the art from the following detailed description of the invention, when considered in conjunction with the accompanying drawings.

The accompanying drawings, which are included to provide a further understanding of the invention, are incorporated in and constitute a part of this specification. They illustrate several embodiments of the invention and, together with the written description, serve to explain the principles of the invention.

Figure 2:
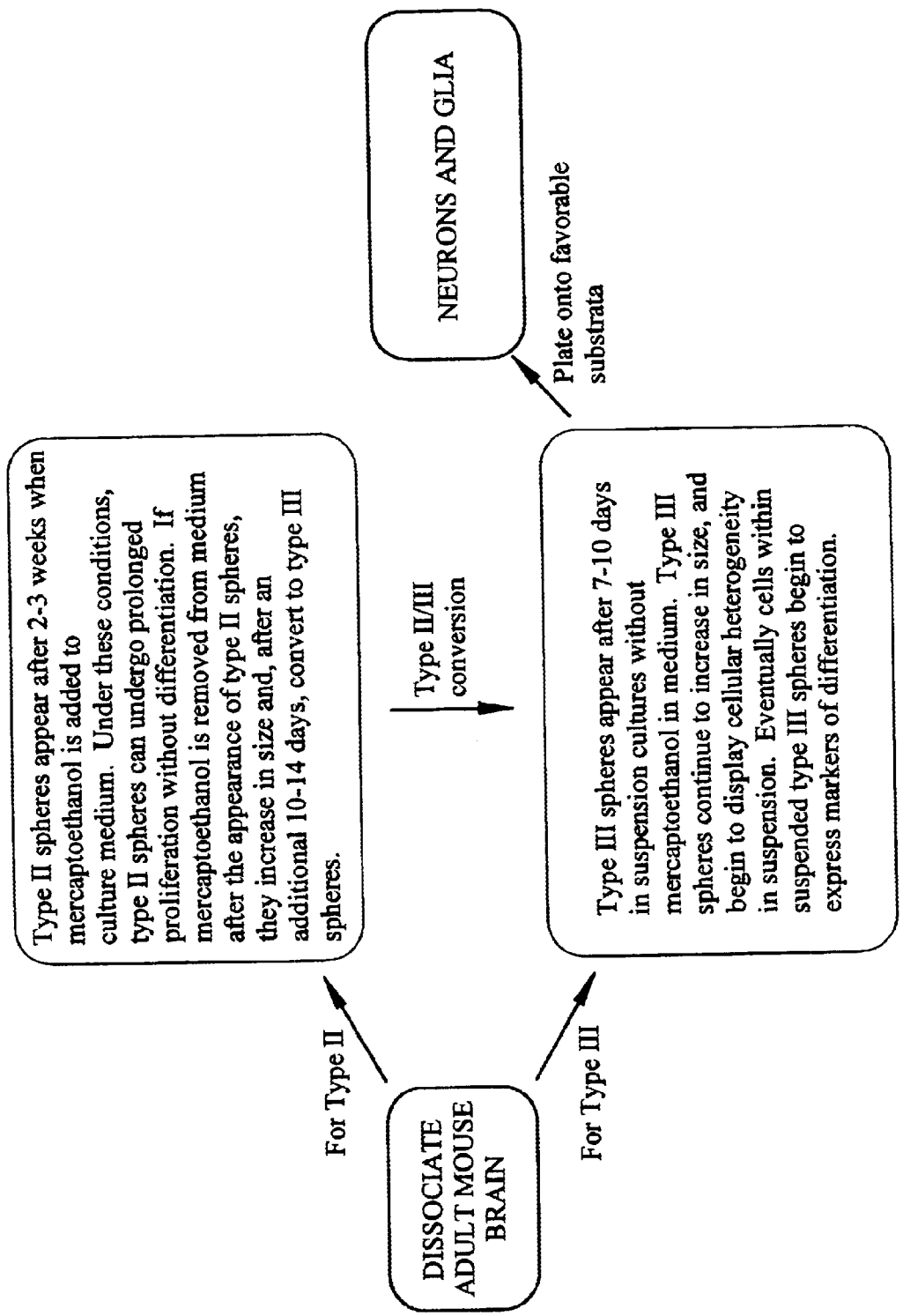

FIGS. 1A–F shows phase contrast and electron microscopic images of type I, II and III clones. FIGS. 1A, 1C, and 1E are phase contrast images of type I, II and III clones of cultured adult brain cells, respectively. FIGS. 1B, 1D, and 1F show type I, II and III spheres counterstained with propidium iodide, respectively. Scale bars for FIGS. 1A–F are 40, 30, 20, 30, 20, and 30 microns, respectively;

FIG. 2 depicts the types of spheres found in the culture paradigm of the invention, and the generation conditions for the appearance and evolution of sphere types from brain;

FIGS. 3A–D shows the phase and electron microscopic images of type II (A and B) and type III (C and D) spheres. Scale bars for FIGS. 3A–D are 10, 5, 15, and 2 microns, respectively;

FIGS. 4A–J shows immunostaining of early and late type II and type III spheres. Scale bars for FIGS. 4A, G and J are 10 microns, FIGS. 4B and 4C are 15 microns, FIGS. 4E and 4F are 30 microns, FIG. 4H is 20 microns, and FIG. 4I is 100 microns;

FIGS. 5A–D shows the evolution and proliferation of type II (FIGS. 5A and 5C), and type III (FIGS. 5B and 5D) spheres. Scale bars for FIGS. 5A and 5B are 25 microns, and for FIGS. 5C and 5D are 10 microns;

FIGS. 6A–B shows type II and type III spheres from ROSA-26 transgenic mice. Scale bars for FIG. 6A is 50 microns, and FIG. 6B is 30 microns; and FIGS. 7A–D shows phase and electron microscopy of a type II adult mouse and type II adult human sphere. The adult mouse sphere is approximately 100 microns in diameter, while the adult human sphere is approximately 200 microns in diameter.

The present invention describes methods which can be used to isolate, amplify, and grow stem/precursor cells from the mammalian brain. By manipulating specific aspects of cell separation and cell adhesion, the invention methods described herein can be used to specifically isolate and culture type I, type II and type III precursor cells. It should be noted that in a recent paper by Kukekov et al. (*Glia,* 21:399, (1997)) the type II and type III cells of the instant invention are referred to as type I and type II cells, respectively, for convenience.

Cell separation and cell adhesion can be manipulated using a variety of contact-limiting and contact-inhibiting factors. For example, chemical-separating agents such as mercaptoethanol, physical separating agents such as methylcellulose, and anti-adhesives such as poly 2-hydroxyethyl methacrylate are used to deter cell-cell and cell-substrate associates during the initial isolation of stem/precursor cells from the newly-dissociated brain. This allows the "purification" of these cells from mature, differentiated neurons and glia that are also dissociated during the brain dissociation procedures. The mature, differentiated neurons and glia cannot survive these anti-adhesion, anticell interaction procedures. Thus, agents such as mercaptoethanol are always used in the first stage of isolation of type I and II clones to help deter the survival of the more mature cellular elements (by deterring their clustering). At the same time, agents such as mercaptoethanol may have certain growth-promoting actions on the single stem/precursor cells that eventually proliferate to form these early sphere types.

Since cell-cell and cell-substrate interactions are important for cellular differentiation, contact-inhibiting (or contact-limiting) factors as mercaptoethanol are eventually removed from the culture medium for the evolution or differentiation of type II and type III spheres. The differentiation of type III spheres requires other additional factors, including growth factors like beta fibroblast growth factor, epidermal growth factor, or such factors that are also contained within pituitary extract. Such additional factors are described in the type III culture media discussed below (see, Example 3).

The adult mammalian brain harbors a discrete, prolific population of primitive stem/precursor cells that possess many of the attributes of stem/precursor cells seen in other organs. Since these earliest (most primitive) cells do not readily attach to culture substrata, and require contact-limiting factors for amplification, they may have been overlooked in previous culture studies of adult brain stem and progenitor cells. Under certain culture conditions, these cells evolve into many different classes of cells, including progenitors that give rise to neurons and different types of glia. In this way, they possess many of the cytological characteristics of hematopoietic stem/precursor cells that can give rise to different types of blood progenitor cells. These brain stem/progenitor cells may be produced on a large scale and can be genetically altered using a variety of transfection methods.

The pluripotential brain cells of the instant invention can be directed to particular neuronal or glial lineages. Thus, the culturing methods of the instant invention can be used to produce large numbers of clonally-related cells of a specific cell type. The methods of producing such large populations of cells as well as the cells themselves are specifically useful in replacing cells that are lost due to disease processes. For example, the production of large quantities of specific glial cells by the methods of the present invention and subsequent transplantation of these glia into the brains of multiple sclerosis patients, would be particularly beneficial to such patients. Similarly, neurons generated from the stem/precursor cells of the instant invention, transplantation of these neurons, and the integration of the activities of the replaced cells into established brain circuitries is particularly useful in brains where neuronal cell loss has occurred. Cells generated using the methods of the instant invention can also be used in the brain or spinal cord for regeneration or space-occupation, as in spinal cord syrinx injuries, or stroke cavities, arteriovenous malformations, epileptic foci, or peripheral nerve neuromas to fill cavities. Large or small scale production of the cells using the invention methods are also useful for drug-discovery and testing.

The culture paradigms described below yield three morphologically and antigenically distinct populations of cellular aggregates, types I, II and III. These populations of cellular aggregates are termed "clones", each clone having distinct characteristics (see, FIG. 1). As shown in FIG. 1A, clones of type I appear as phase-bright, very small dense bodies. It is not possible to discern individual cells within the clones using phase microscopy. However, when the cells are counterstained with propidium iodide (PI) (see, FIG. 1B), type I clones exhibit areas of very small, punctate staining interspersed with regions that lack staining. Type I clones do not appear to attach to either plastic or laminin-coated substrates, and cells of individual clones are not separable by trypsinization. Furthermore, type I clones are immunonegative for all of the cell-specific markers tested so far.

Type II clones from adult mouse and human brain dissociations, spontaneously appear in suspension cultures (see FIGS. 1C, 1D, 3A, and 3B), containing at least one contact-limiting or contact-inhibiting factor. Some exemplary contact limiting factors include, but are not limited to, mercaptoethanol, poly 2-hydroxyethyl methacrylate, and methylcellulose. Mercaptoethanol functions as a chemical-separating agent as it breaks disulfide linkages of proteins which are involved in cell-cell and cell-substrate interactions. Methylcellulose functions as a physical separator; it is a viscous bioorganic solution which, by its viscous nature, limits contacts between cells and between cells and a substrate, and allows clonal analyses. Poly 2-hydroxyethyl methacrylate functions as an anti-adhesive for substrate coating. This prevents cell contact with adhesive surfaces and also prevents differentiation. Other compounds or procedures which function to limit or inhibit cell-cell and cell-substrate interactions can also be used with this invention. Culturing as a suspension also deters cell-cell and cell-substrate contacts with higher yields of spheres, but culturing in methylcellulose again, allows clonal analyses.

In contrast to type I clones, type II clones are phase-dark, spherical bodies that become larger with time (FIGS. 1C and 3A). Electron Microscopy (EM) revealed that type II clones consist of rings of small, tightly apposed cells that surround a core of flocculent, non-cellular material having many characteristics of extracellular matrix (FIGS. 1D and 3B). The type II cell has many organelles, including endoplasmic reticulum, Golgi apparatus, dense bodies, and mitochondria. The closed arrow in FIG. 1C points to a multisphere aggregate (as shown by propidium iodide counterstaining, a DNA stain for cell nuclei, in FIG. 1D). The closed arrow in FIG. 1E points to a type II sphere residing near a type III sphere, which is marked by an open arrow.

Type II clones do not attach to either plastic or laminin-coated substrates. Immediately after they appear in culture, type II clones are immunonegative for cell-specific markers, including GFAP (glial fibrillary acidic protein, which labels more mature and reactive astrocytes), nestin (RAT401, which stains neurepithelial stem cells as well as radial glia), and TuJ1 (which stains class III β-tubulin that is expressed in recently postmitotic (committed) as well as mature neurons in the CNS). However, after approximately ten days to two weeks in vitro, some cells of type II clones (late type II, or early type III) become immunopositive for nestin, but remain immunonegative for GFAP and TuJ1 (see, FIG. 4). If the factors that inhibit cell contact are removed from the medium, provided the type II clones are not kept in the contact-limiting factor for more than two weeks, type II clones will convert to type III clones.

In contrast to type II clones, type III clones, when plated on plastic or laminin-coated substrates, attach readily, and produce a number of process-bearing cells that migrate away from the sphere to from a single layer of cells. Type III cells are immunopositive for a variety of cell-specific markers, including GFAP, nestin, L1 (a marker of an adhesion molecules that is on the surface of neurons and their processes), and TuJ1 (see, FIG. 4). Some cells exhibit very light, punctate staining using an antibody to the 04 antigen (marker of oligodendrocytes).

In addition to the type I, type II and type III clones, the primary cultures of the instant invention also appear to initially contain differentiated neurons and glia. However, in the presence of contact-inhibiting factors, neurons and astrocytes were not immunologically detected after 1 week; they presumably cannot survive under these culture conditions.

The culture paradigm of the invention, and the generation conditions for the appearance and evolution of sphere types from a brain are depicted in FIG. 2. Both type II and type III stem/precursor cells are generated from a dissociated adult mammalian brain. Type II cells appear 2–3 weeks after mercaptoethanol, or other cell contact limiting factor, is added to the culture medium. When mercaptoethanol, or other contact-limiting factor, is subsequently removed from the medium after the appearance of type II spheres, the type II spheres increase in size and, after an additional 10–14 days, convert to type III spheres. In addition to developing from type II clones after the addition and subsequent removal of a contact limiting factor, type III clones can also appear spontaneously in suspension cultures grown in the absence of contact limiting factors.

Figure 3:
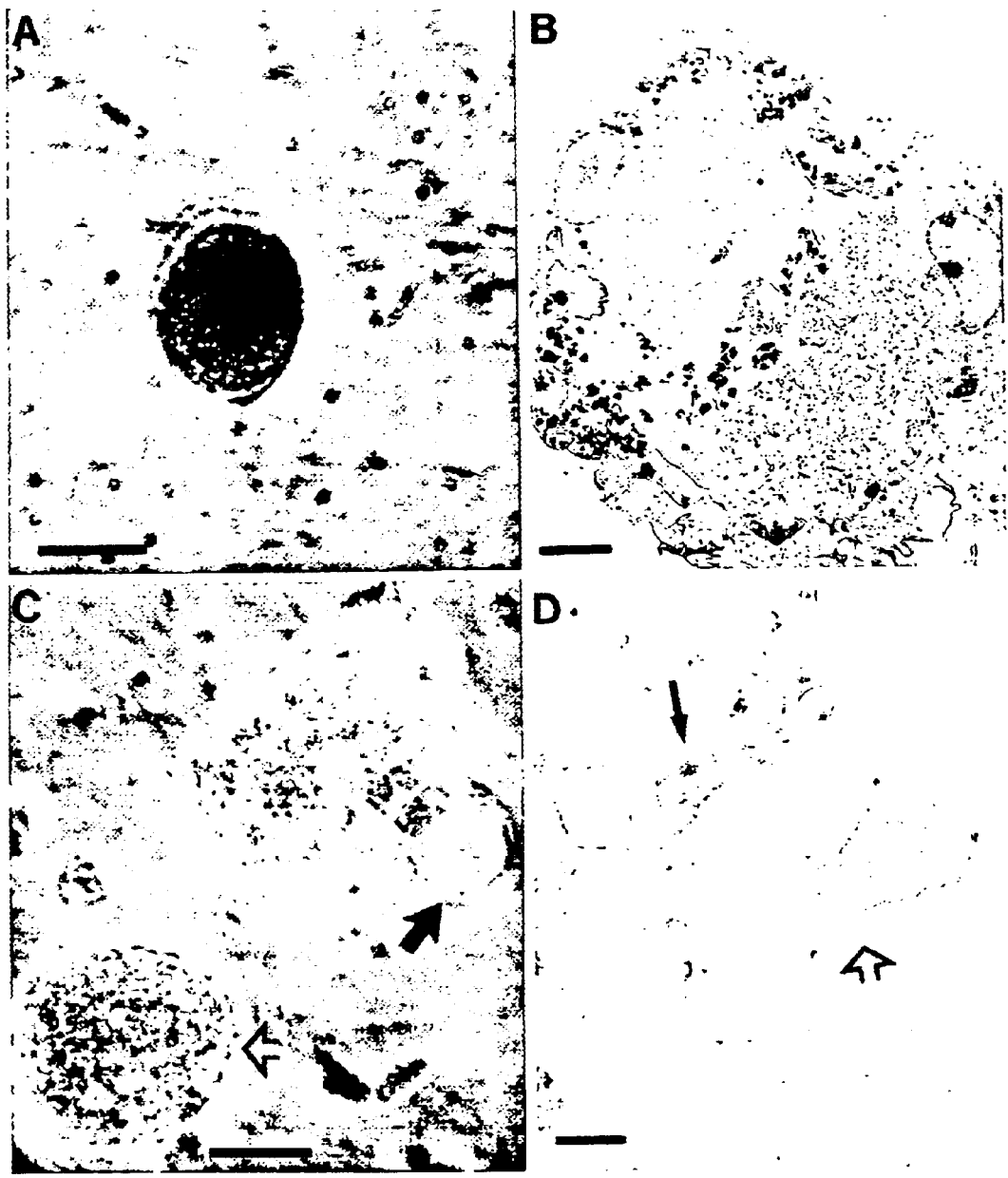

FIG. 3 shows the phase and electron microscopic images of type II (A and B) and III (C and D) spheres. After approximately 30 days in vitro, type II clones take on characteristics of type III clones. The size of the type II clones increase dramatically, and their color changes from phase-dark (FIGS. 1C and 3A) to phase-bright (FIGS. 1E and 3C). In addition, large cells appear at the edges of the type III clones.

FIG. 3C shows type III spheres which are generally larger and phase-brighter than type II spheres. The open arrow points to a late type II or early type III sphere, and the closed arrow points to a large cellular protrusion on the periphery of a late type III sphere which appears brighter than the early type III, and has a more irregular border due to many protrusions. FIG. 3D shows cells of type III spheres which look more mature than type II cells. The open arrow points to a large cell, and the closed arrow marks a smaller cell with a darker nucleus.

Type III spheres will continue to increase in size and begin to display cellular heterogeneity when grown in suspension culture. Eventually, cells within suspended type III spheres begin to express markers of differentiation. Such cells can eventually become neurons and glia when plated onto favorable substrata such as laminin/poly ornithine coated surfaces, polylysine, or plastic, or other matrix molecules, or transplanted into a host brain.

Figure 4:
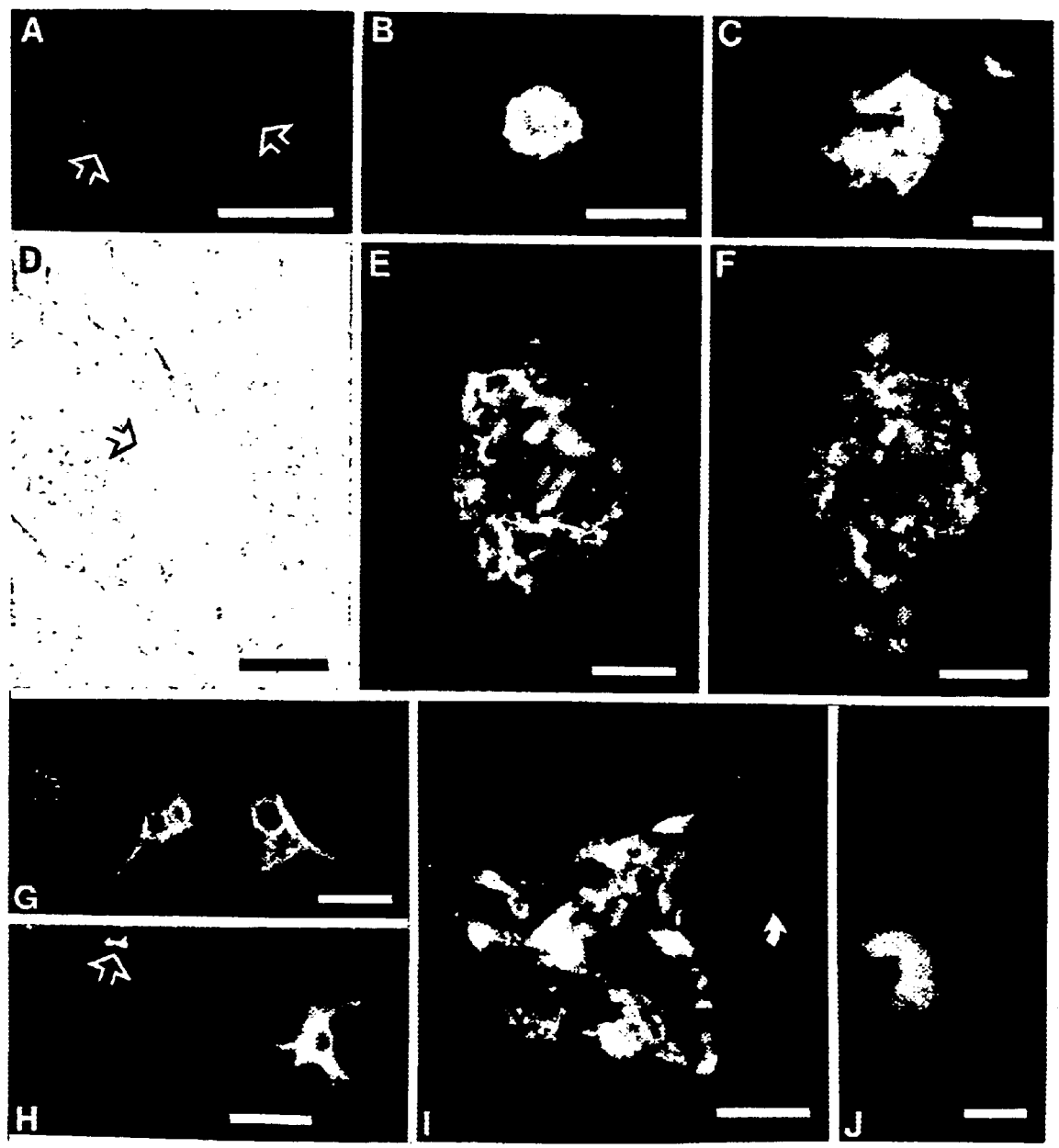

FIG. 4 shows the immunostaining of early and late type II and III spheres illustrating that the various characteristics of the type II and type III spheres can be readily distinguished from their immunostaining profiles and their phase-contrast, and EM images. Early type II spheres are shown in FIG. 4A. The open arrows point to two type II spheres that abut each other. These spheres are negative for the putative stem cell intermediate filament protein, nestin. A more mature type II sphere that is immunopositive for nestin is shown in FIG. 4B. FIG. 4C shows an early type III sphere immunopositive for nestin, with some unlabeled cells also apparent. FIG. 4D shows a phase contrast image of a late type III sphere (open arrow) showing processes after attaching to plastic. FIGS. 4E and 4F show a type III sphere, with cells beginning to disperse after attaching to plastic. This sphere is double immunostained for GFAP (FIG. 4E) and β-III tubulin (FIG. 4F). FIG. 4G depicts astrocytes and shows that dispersed cells of type III spheres are immunopositive for nestin. FIG. 4H shows astrocytes from dispersed type III spheres also stain for GFAP. The open arrow points to a morphologically different astrocyte than the large cell on the right. FIG. 4I shows cells that are dispersed from an attached type III sphere and which are immunopositive for L1. The arrow points to a long L1-positive process. FIG. 4J shows a single cell immunopositive for β-tubulin, counterstained with propidium iodide (orange), after attachment of a type III sphere. Thus, type II and type III spheres are easily distinguishable from each other, not only by the differences in phase contrast, and EM images, but also by their distinct immunostaining profiles.

Figure 5:
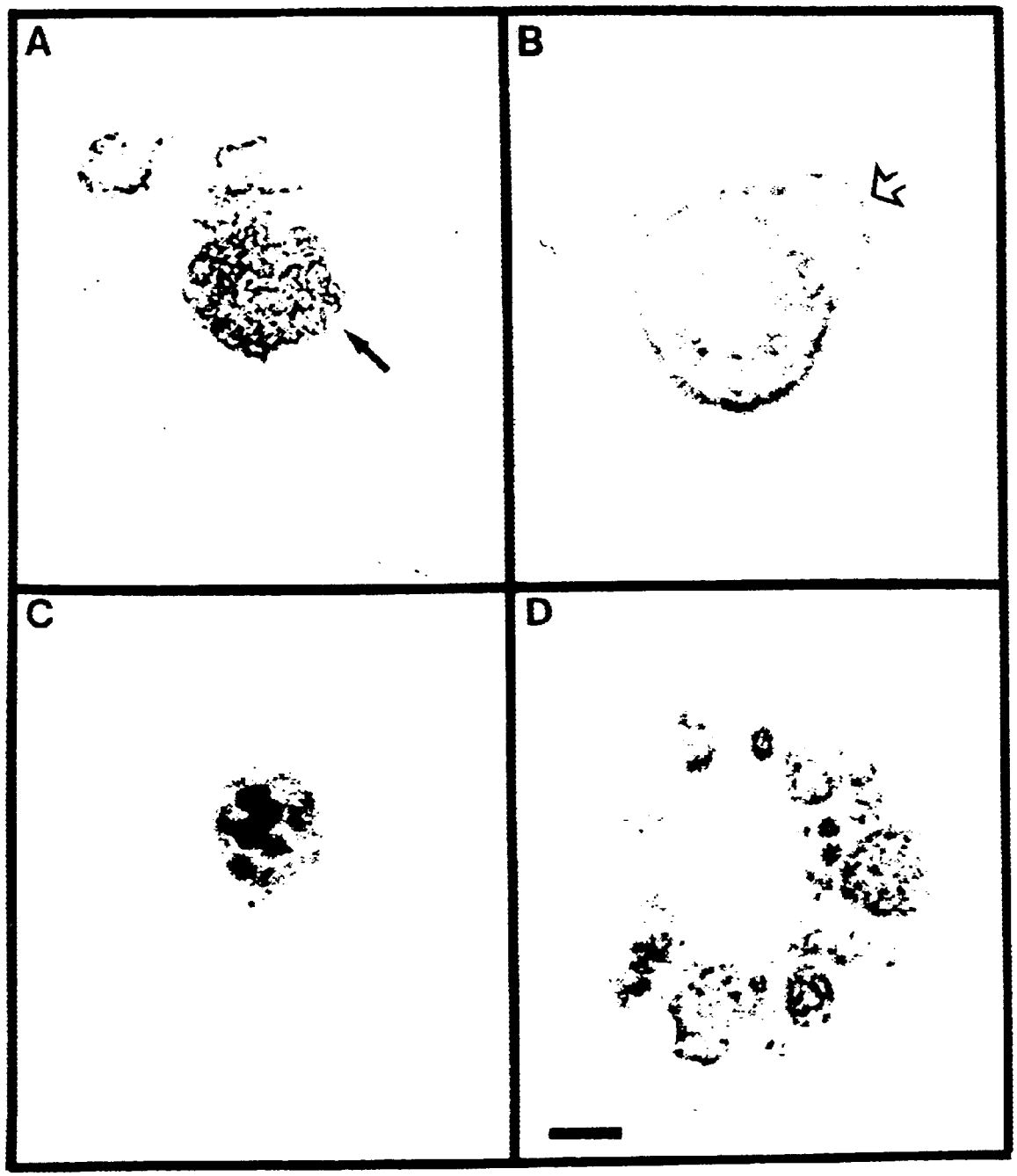

The evolution and proliferation of a type II sphere differentiating into a type III sphere can be seen in FIG. 5. A single late type II sphere (arrow in FIG. 5A) was followed in suspension culture with phase microscopy. After 10 days, this type II sphere had increased in size and altered its morphology to become the type III sphere shown in FIG. 5B. The open arrowhead points to a cellular protrusion on the edge of the sphere typical of the type III sphere. Cellular debris around the type II sphere in FIG. 5A is absent from the type III sphere in FIG. 5B due to movement during feeding. Heterogeneous cultures of spheres exposed to a 20 hour pulse of BrdU reveal proliferative cells in both type II (FIG. 5C) and type III (FIG. 5D) spheres. Notice that both the small sphere in FIG. 5C and the larger sphere in FIG. 5D contain labeled nuclei with a variety of sizes. This indicates that there may be different progenitor cells types proliferating in the spheres; some progenitor cell types giving rise to neurons, some giving rise to glia.

Removal of the contact inhibiting factors will allow differentiation to occur. In addition, the type II and type III growth media containing growth factors such as basic fibroblast growth factor (bFGF), or epidermal growth factor (EGF) encourages differentiation. Other growth factors such as brain-derived neurotrophic factor (BDNF), glial derived neurotrphic factor (GDNF), NT3, and ciliary neurotrophic factor (CNTF) may also encourage differentiation of the stem/precursor cells.

It should also be noted that the flat, spread appearance of the type III sphere in FIG. 5D is probably due to this sample being taken from a 96 hour culture as opposed to the 48 hours for the type II sphere, and type III spheres have a tendency to spread and migrate when attached. The lack of spreading of the type II sphere may also account for the higher level of background staining.

Figure 6:

Type II and type III clones were also generated from ROSA-26 mice, a strain that expresses the β-galactosidase transgene in all cell types, to perform transplant experiments. ROSA-26 transgenic mice are commercially available from the Jackson Laboratories, Bar Harbor, Me. The results show that following transplantation into adult mouse brain, type II and type III clones can survive and differentiate. (FIG. 6). When these β-galactosidase positive type II and type III clones were transplanted to the striatum of adult ICR mice, small and large X-gal positive cells were found to survive up to two weeks. Moreover, immunocytochemistry with GFAP revealed the presence of labeled astrocytes and non-labeled larger cells (presumably neurons). FIG. 6A shows a β-galactosidase positive late type III sphere (large open arrow), and unlabeled early (right open arrowhead) and late (left open arrowhead) type II spheres. The filled arrow points to unidentified labeled elements out of the plane of focus. FIG. 6B shows the combined bright field/fluorescence image of a transplant of type II and III spheres into the striatum of an adult ICR mouse. Surviving astrocytes marked with a filled arrow are counterstained for GFAP. Large GFAP-negative, β-galactosidase-positive cells, presumed to be neurons (open arrow), are also seen. Other transplanted cells can be seen within this host brain structure as well. Immunofluorescence is yellow; the β-galactosidase product is blue-green. These results support the conclusion that the novel stem/precursor cells are useful in regeneration following neurological cell damage.

Figure 7:
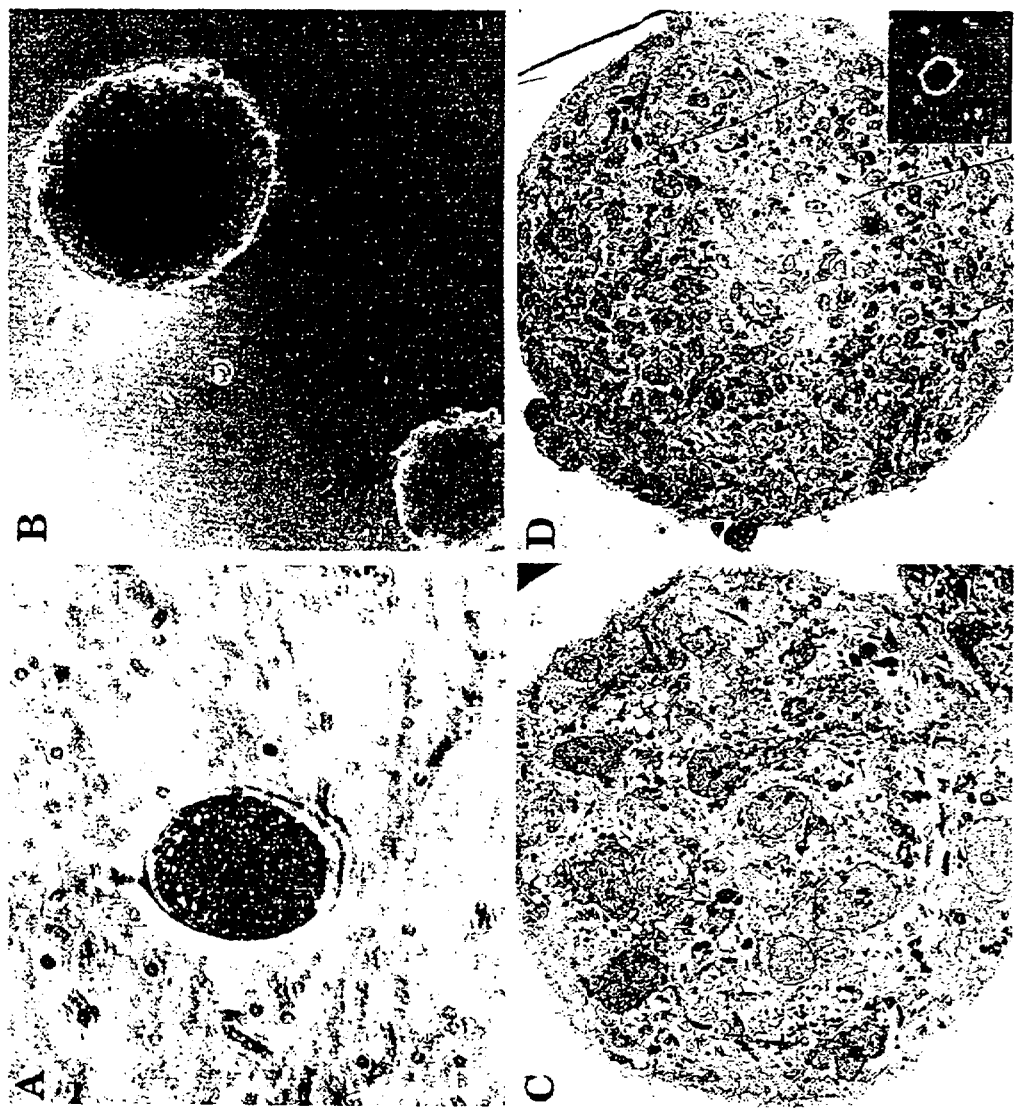

Type II and type III clones were also generated from the adult human brain, and from dead animals with long post-mortem intervals when the animals were kept at 4° C. (see, FIG. 7). FIG. 7 shows phase and electron microscopic images of type II adult mouse and human spheres. FIG. 7A shows the phase microscopic image of a type II adult mouse sphere that looks similar to a sphere with a postmortem interval of 0 hours, while FIG. 7B shows the phase microscopy of a type II sphere from an adult mouse with a postmortem interval of sixteen hours. FIG. 7C shows the electron microscopic image of a type II sphere from an adult transgenic mouse (tenascin glycoprotein knockout mouse). A complex cellular aggregate can be seen. This sphere is approximately 100 microns in diameter. FIG. 7D shows the electron microscopy of an adult human sphere (as shown in the inset, a phase microscopic image of a type II sphere). Similar to the electron microscopy of a type II sphere from an adult transgenic mouse (FIG. 7C), this human sphere (FIG. 7D) also shows a complex cellular aggregate. This human sphere is approximately 200 microns in diameter.

The different types of clones observed in the cultures described above and in the experiments described below, represent a continuum of cell proliferation and differentiation, with the existence of both early and late type II clones, which can be compact or loose in appearance, based on cell packing density, that eventually differentiate into type III clusters (see FIGS. 1 and 3). The potential for numerous, undefined hematopoietic stem cells still exists (see, for example, Larochelle et al. *Nature Med.*, 2:1329–1337 (1996)). The identification and understanding of neuropoietic stem and progenitor cells based on a combination of morphology, gene marking, and unique biochemical features, such as that described herein, ensure reliability in the results. The use of just one feature as an identification tool can occur, although it makes the recognition of the specific stem cell type rather tenuous.

While the inventors do not wish to be bound by any particular theory, neuropoiesis in the adult brain is probably a rather limited event, based on current knowledge of hematopoiesis and the presence of stem cells in other tissues, as well as the apparent existence of a quiescent population of so-called stem cells in the SEZ (see, Potten et al. *Development*, 110:1001–1020 (1990); and Morshead et al., *Neuron* 13:1071–1082 (1994)). For this reason, methods that amplify the ex vivo production of these cells, as described herein, are useful to generate large numbers of such cells for classification and transplantation. Furthermore, the methods of the instant invention can be applied to harvesting the small number of stem/precursor cells from adult brains, particularly adult brains with significantly long postmortem intervals (e.g. 1 day), allowing the "banking" of these cells for future studies and cell-replacement therapies.

Also, novel approaches as described here, that uncover either novel stem/precursor cells or aspects of their growth and differentiation that lead to classification of stages of adult brain neuropoiesis are also useful. The described methods allow this process with the production of the most primitive stem/precursor cells, and facilitate the generation and analyses of a continuum of developing and differentiating brain stem/precursor cells.

The culture conditions of the present invention involve limiting cell-cell and cell-substrate interactions leading to the enhanced production of spheres of type II and III cells. Since previous studies have only shown a dense extracellular matrix within the SEZ in vivo (see, for example, Gates et al., *J. Comp. Neurol.*, 361:249–266 (1995); and Thomas et al., *Glia.* 17:1–14 (1996)), and since ECM molecules have been reported to affect the proliferation and differentiation of hematopoietic stem cells (see, for example, Klein et al., *J. Cell Biol.*, 123:1027–1035; and Yoder et al., *Exp. Hematol.*, 23:961–967 (1995)), and while the inventors do not wish to be bound by any particular theory, it is presumed, that the methods of the present invention affect the actions of the ECM molecules, adhesion proteins, growth factors and their interactions. Preliminary studies using immunocytochemistry and the reverse transcriptase polymerase chain reaction (rtPCR) suggest that sphere cells express transcripts as well as protein of particular ECM molecules (e.g. tenascin).

As described above, the appearance of two types of proliferating cells that form neurosphere-like aggregates from dissociated adult brain, termed type II, and III clones, were consistently observed. While the type III clones in the culture paradigm of the invention most likely represent neural progenitor cells that have previously been described in the aforementioned papers (see, for example, Reynolds et al., *J. Neurosci.*, 12:4565–4574 (1992); Reynolds et al., *Dev. Biol.*, 175:1–13 (1996); and Weiss et al., *J. Neurosci.*, 16:7599–7609 (1996), all cited above), it has been heretofore unrecognized that such type III spheres are derived from the type II precursors of the instant invention. By isolating and amplifying type II spheres in specific culture conditions, type III spheres can be obtained. In addition, prior to the disclosure of the methods of the instant invention, type II and type III spheres have not been previously obtained from post-mortem brain specimens.

In addition, prior art stem cells are not as primitive as the type II stem cells of the present invention as evidenced by the fact that the prior art stem cells are all nestin-positive. The type II clones of the instant invention represent a truly unique, ontogenetically earlier form of stem/progenitor than those previously described. This conclusion is supported by data showing that the type II clones are first initially nestin-negative, followed by a progression through a nestin-positive state to become a type III clone, and finally differentiation into neurons or glia (see, FIGS. 2–4).

The following examples are offered by way of illustration and are not intended to limit the scope of the claimed invention.

EXAMPLE 1

The Production of Type I Clones

Adult ICR or transgenic or mutant mice, or biopsy specimens from human temporal lobe (for epilepsy surgery), or brain specimens with significant (i.e. at least one day) postmortem intervals, were used as tissue sources for dissociations. The brains were dissociated and cultured follows. Extracted brain tissues were minced with a razor blade and washed in a mixture of ice-cold DMEM (Dulbecco's modified Eagle's medium, commercially available from a variety of vendors) and any antibiotic-antimycotic product such as Sigma Chemical Co. Catalogue #A5955 (100×). (Such antibiotic-antimycotic products are also commercially available from Gibco Brl, Grand Island, N.Y.). Brain pieces were transferred to a beaker containing 0.25% trypsin and EDTA (ethylenediaminetetraacetic acid) and mixed on a magnetic stir-plate for 15 minutes, triturated with a plastic pipette, filtered through sterile gauze, and collected in a 15 ml tube and centrifuged for 5 minutes at 1200 rpm. Cells were resuspended in DMEM/F12 medium+N1 supplement (a standard tissue culture medium available from a variety of vendors) plus 5% FBS (fetal bovine serum) and grown in suspension cultures by plating at high density on a non-adhesive substrate (tissue culture plastic coated with poly 2-hydroxyethyl methacrylate; Sigma Chemicals). Cells were fed every 3–4 days by centrifugation and resuspension in fresh medium.

The basic media for culturing type I cells comprises the following ingredients: Insulin (5 µg/mL), putrescine (100 µM), progesterone (20 µM), sodium selenite (30 µM), pituitary extract (20 µg/mL), transferrin (100 µg/mL), and 5% fetal calf serum (FCS) in DMEM/F12 media.

Type I cells only appear in suspension cultures containing a non-adhesive substrate such as poly 2-hydroxyethyl methacrylate. Some type II cells are also present in these cultures.

EXAMPLE 2

The Production of Type II Clones

Type II clones, similar to type I clones, were obtained from adult ICR, transgenic or mutant mice, or biopsy specimens from human temporal lobe (for epilepsy surgery). In addition, Type II clones were also generated from the adult human brain, and from dead animals with long post mortem intervals when the animals were kept at 4° C.

The brains were dissociated and cultured as previously described for the generation of type I clones. Briefly, extracted brain tissues were minced, washed, and transferred to a beaker containing 0.25% trypsin and EDTA. After being mixed on a magnetic stir-plate for 15 minutes, the culture was triturated with a plastic pipette, filtered through sterile gauze, centrifuged, and resuspended in DMEM/F12 medium+N1 supplement, plus 5% FBS, plus 20 µg/mL pituitary extract (from Gibco) and grown in suspension cultures by plating at high density on a non-adhesive substrate.

Cells were plated and fed as described above for the type I cells. However, the basic media described above (comprising insulin (5 µg/mL), putrescine (100 µM), progesterone (20 µM), sodium selenite (30 µM), pituitary extract (20 µg/mL),transferrin (100 µg/mL), and 5% fetal calf serum (FCS) in DMEM/F12 media) also contained 10 ng/mL basic fibroblast growth factor (bFGF), and 10 ng/mL epidermal growth factor (EGF). Importantly, the culture media additionally contained 100 µM mercaptoethanol as a contact-limiting factor that reduces disulfide bonds (See, E. C. Herrington, *Biochem. Pharmacol.*, 35:1359–1364 (1986).) Cultures contained dense debris for 10–14 days. Mercaptoethanol was then removed from the medium after 10–14 days. Clones of type II were present in these cultures. Some type III clones were also present.

EXAMPLE 3

The Production of Type III Clones

Similar to the type I and type II clones, Type III clones were obtained from adult ICR, transgenic or mutant mice, or biopsy specimens from human temporal lobe, or from the adult human brain, or from dead animals with long post mortem intervals when the animals were kept at 4° C. The brain source was dissociated as described in Examples 1 and 2 above, and the cells were grown in the suspension culture described above either without contact inhibiting factors, or, more often with a contact inhibiting factor such as mercaptoethanol. The basic media for culturing type III cells was the same as that used for culturing type II cells. Namely, the media comprised insulin (5 µg/mL), putrescine (100 µM), progesterone (20 µM), sodium selenite (30 µM), pituitary extract (20 µg/mL), transferrin (100 µg/mL), 10 ng/mL basic fibroblast growth factor (bFGF), 10 ng/mL epidermal growth factor (EGF), and 5% fetal calf serum (FCS) in DMEM/F12 media. Cells were fed every 3–4 days by centrifugation and resuspension in fresh medium. After removal of the contact limiting factor, both type II and Type III clones were apparent after 5–7 days. The type II clones eventually evolved into type III clones upon continued culturing in the absence of contact limiting factors.

Simply removing the contact inhibiting factors encourages differentiation by encouraging cell-cell contact. However, differentiation of type III clones into neurons or glia is also encouraged by other additional factors, including the growth factors like β-fibroblast growth factor, epidermal growth factor, or factors that are contained within pituitary extract present in the basic type III culture media. Other growth factors such as brain-derived neurotrophic factor (BDNF), glial derived neurotrphic factor (GDNF), NT3, and ciliary neurotrophic factor (CNTF) may also encourage differentiation of the stem/precursor cells.

The following chart summarizes the various methods to obtain the different stem/precursor cell types of the instant invention:

| Steps | Type I clones | Type II clones | Type III clones | |
|---|---|---|---|---|
| Brain dissociation | + | + | + | + |
| Grow in suspension Culture | + | + | + | + |
| Add contact inhibiting factor (for ≦ 2 weeks) | + | + | + | |
| Remove contact inhibiting factor | | + | + | |
| Culture or plate on plastic/laminin coated substrate | | | + | + |

EXAMPLE 4

Fixing of Cultures for Staining or Antibody Testing

Cultures are fixed in one of two ways depending upon the cultivation paradigm. Adherent clones (cultivated on plastic or laminin-coated plastic) are washed three times with room temperature Dulbecco's PBS (phosphate buffered saline) and then fixed either with 10% acetic acid in pure ethanol at −20° C., or ice cold 4% paraformaldehyde in PBS. After 3/4 to 1 hour, the fixative was removed and the cultures were washed three times with PBS.

Clones cultivated as suspension cultures were collected in a 15 ml plastic tube and centrifuged to form a pellet. Culture medium was aspirated and fixative (described above) was added to the pellet. Clones were then triturated and kept in fixative for 3/4 to 1 hour, after which time the cells were again centrifuged and washed in PBS. Finally, the pellet was resuspended in a small volume of fresh PBS, and small aliquots of cells were placed on polylysine-coated coverslips and allowed to dry before the application of cellular stains or antibodies.

EXAMPLE 5

Preparation of Cultures for Ultrastructural Analysis

Clones grown in suspension cultures were prepared for ultrastructural analysis by fixation in sodium cacocodylate buffer comprising 2% glutaraldehyde, 2% paraformaldehyde, 0.5% acroline, and 5% sucrose. The fixative was warmed to 37° C. and gradually added to cultures until the fixative-to-medium ratio was 1:1. Cells were then collected in 15 ml tubes and centrifuged to form a pellet which was then covered with 100% fixative for several hours before processing with standard embedding, staining, and sectioning protocols. Samples were viewed on a JEOL 2000 electron microscope.

EM of type II clones revealed rings of small, tightly apposed cells that often surround a core of flocculent, non-cellular material (see, FIG. 3B) having many of the characteristics of extracellular matrix. The type II cell has many organelles, including endoplasmic reticulum, Golgi apparatus, dense bodies, and mitochondria.

EM of type III clones (see, FIG. 3D) revealed cells that appear to be more differentiated than type II cells, as their cytoplasm is less dense than type IIs and their organelles appear to be more developed. FIG. 7 shows EM of a clone from a transgenic mouse (tenascin knockout mouse) and a sphere (clone) from an adult human temporal lobectomy specimen.

EXAMPLE 6

Culturing of Cells in Methylcellulose for Observation of Single Clones

Methylcellulose (StemCell Technologies, Vancouver, B.C.) was dissolved in medium (o a concentration of 1.6%, and Dulbecco/F12 +N1 supplement medium was added, with an equal volume of brain cells suspension, to a final concentration of 0.8% methylcellulose (see, Worton et al., J. Cell Physiol., 74;171–182 (1969)). Cells were fed every 2–3 days by the addition of small aliquots of medium without methylcellulose. Single clones were followed over time (see, FIG. 5), and observed to increase in size indicating cell proliferation and growth.

EXAMPLE 7

Testing Clones for Reactivity to Cell Markers

Standard immunofluorescence techniques were used with antibodies to polyclonal GFAP (Immunon), monoclonal β-tubulin (Sigma), polyclonal L1 (gift of Professor Melita Schachner), monoclonal nestin (Developmental Hybridoma Bank), and 04 (Chemicon). Cells were also labeled with propidium iodide (Sigma).

Type II clones are immunonegative for cell-specific markers, including GFAP, nestin, and TuJ1. These are considered early type II clones. However, after approximately 10 days in vitro, some cells of type II clones become immunopositive for nestin but remain immunonegative for GFAP and TuJ1. Type III clones exhibit cell phenotype markers of more differentiated cells being immunopositive for nestin, GFAP, L1, and TuJ1. This staining pattern shows the continuum of evolution of type II clones from early (immunonegative) to late (selectively immunopositive) and eventually to type III clones (fully immunopositive) (see, FIG. 5).

Other techniques can be used to distinguish type II and type III clones. For example, rtPCR can be used to reveal genes that are different between type II and type III clones. Not only will this further characterize the type II and type III clones, but it will also reveal novel genes in each clone type, as well as identify genes involved in different developmental stages of neuronal precursor cells.

EXAMPLE 8

Using Brains from Dead Mammals as a Source of Stem/Precursor Cells

Using exactly the same procedures as outlined for generating type I, II and III spheres from acutely dissociated brain tissue, it is also possible to generate type I, II and III clones from brain tissue of animals with significantly long postmortem intervals (FIG. 7B). Thus far, dissociated brain from adult mice with postmortem intervals from 16–24 hours have yielded normal type I, type II, and type III spheres. Pilot studies have indicated that it might be possible to harvest brain tissue (if stored at 4° C.) from animals or human cadavers with postmortem intervals of up to 2–5 days. These findings have implications for "banking" of mature human brain tissue specimens for experimentation as well as transplantation for traumatic injuries and neurological disease.

EXAMPLE 9

Light and Electron Microscopy of Clones from Adult Human Brain

Human brain also generates type II, and III clones, as described for the adult rodent. Dissociating biopsy specimens from the adult human temporal lobe yields type II, and III spheres using the same culture methods as described for isolating type II and type II spheres from rodent brain tissue. In addition, similar to the adult rodent, human brain may also generate type I clones. FIG. 7D shows human spheres at the light and electron microscopic level that have many of the same cytological feature as described in rodent spheres.

EXAMPLE 10

Transplantation (Grafting) of Type I or II Clones from ROSA-26 Adult Mice

Type II or III clones, generated as described in Examples 2 and 3 (see, above) from adult ROSA-26 transgenic mice (see, Friedrich et al., Genes Dev., 5:1513–1523 (1991)), were aspirated, with media, into a Hamilton microsyringe with an attached 31 gauge needle using a video stereomicroscope set-up. 1 μl was slowly injected into the adult ICR mouse striatum. For stereotaxic coordinates, as well as details for the histochemical detection of β-galactosidase activity, see Gates et al., Neuroscience, 74:579–597 (1996)). Type II and III clones were also found to exhibit X-gal labeling in vitro (see, FIG. 6). Survival times of 7–14 days were observed thus far, with a 10-day survival shown in FIG. 6. It is possible that the transplants can survive longer times, simply carrying the experiment out for a longer time point will determine that. Preliminary studies also indicate that grafted type II and III spheres from adult human brains give rise to cells that survive in the mature brains of immunocompromised mice.

In addition, the transplants can differentiate into different types of resident neuronal populations. For example, some of the transplanted spheres from β-galactosidase-positive mice differentiate into astrocytes in the host ICR (non-β-galactosidase-positive brain); some transplanted spheres differentiate into neurons. Immunocytochemistry with GFAP revealed the presence of labeled astrocytes and non-labeled larger cells that are presumed to be neurons. Furthermore, in vitro cultures using feeder cells from different parts of the body (i.e. endothelial cells, lung endothelial cells, or kidney cells), change the gross morphology of the spheres generated. Both of these in vitro, and in vivo experiments suggest that the environment into which the spheres are transplanted contributes to the type of cells into which they will differentiate. It may therefore be possible to direct the phenotype of the precursor/stem cells using cell feeder layers from specific tissues, as well as other molecular priming approaches, and genetic manipulations (e.g. transfections, or viral infections).

The transplant studies described above were performed in "normal" brain circuitries. Such studies indicate that type II, and III spheres give rise to glia and neuronal cells that can survive the grafting procedure. Similar experiments can be done in compromised circuitries to determine whether or not compromised circuitries result in any lineage restriction or allow further differentiation.

It will be apparent to those skilled in the art that various modifications and variations can be made in the methods of the present invention without departing from the spirit or scope of the invention. Thus, it is intended that the present invention cover the modifications and variations of this invention provided they come within the scope of the appended claims and their equivalents.

We claim:

1. A method for obtaining a purified population of primitive human brain stem cells, comprising culturing dissociated human brain cells on a non-adhesive substrate in suspension culture supplemented with fetal bovine serum and methyl cellulose, where culturing under conditions that inhibit cell-cell and cell-substrate interactions results in a substantially homogeneous population of pluripotent brain stem cells that are immunonegative for glial fibrillary protein, nestin and TuJ1 and are free from mature, differentiated neurons and glia.

* * * * *

UNITED STATES PATENT AND TRADEMARK OFFICE
CERTIFICATE OF CORRECTION

PATENT NO. : 6,638,763 B1
DATED : October 28, 2003
INVENTOR(S) : Steindler et al.

It is certified that error appears in the above-identified patent and that said Letters Patent is hereby corrected as shown below:

<u>Title page,</u>
Item [75], Inventors, replace "Kukekou" with -- Kukekov --.

Signed and Sealed this

Fifteenth Day of June, 2004

JON W. DUDAS
*Acting Director of the United States Patent and Trademark Office*